US012629092B2

(12) United States Patent
Levin et al.

(10) Patent No.: US 12,629,092 B2
(45) Date of Patent: May 19, 2026

(54) PORTABLE AUTOMATED LIFE-SAVING SYSTEM WITH DYNAMIC ADAPTATION

(71) Applicant: CPR Robotics Ltd., Ramat Yishai (IL)

(72) Inventors: Chanoch Levin, Ramat Yishai (IL); Danny Knafou, Lehavim (IL)

(73) Assignee: CPR ROBOTICS LTD., Ramat Yishai (IL)

( * ) Notice: Subject to any disclaimer, the term of this patent is extended or adjusted under 35 U.S.C. 154(b) by 667 days.

(21) Appl. No.: 17/908,753

(22) PCT Filed: Mar. 2, 2021

(86) PCT No.: PCT/IL2021/050235
§ 371 (c)(1),
(2) Date: Sep. 1, 2022

(87) PCT Pub. No.: WO2021/176451
PCT Pub. Date: Sep. 10, 2021

(65) Prior Publication Data
US 2023/0128620 A1      Apr. 27, 2023

Related U.S. Application Data

(60) Provisional application No. 62/983,805, filed on Mar. 2, 2020.

(51) Int. Cl.
*A61B 5/00*        (2006.01)
*A61B 5/0245*      (2006.01)
*A61N 1/39*        (2006.01)

(52) U.S. Cl.
CPC .......... *A61B 5/4836* (2013.01); *A61B 5/0245* (2013.01); *A61N 1/39044* (2017.08);
(Continued)

(58) Field of Classification Search
CPC .......................... A61N 1/39044; A61N 1/3987
See application file for complete search history.

(56) References Cited

U.S. PATENT DOCUMENTS 10,610,111 B1    4/2020  Tran
2002/0026131 A1*  2/2002  Halperin .............. A61H 31/006
                                                        601/41
(Continued)

FOREIGN PATENT DOCUMENTS

CN        102872486 A      1/2013
CN        102043894 B      9/2014
(Continued)

OTHER PUBLICATIONS

Supplementary European Search Report for Application No. 21764887.2 dated Mar. 4, 2024.
(Continued)

*Primary Examiner* — Joseph D. Boecker
*Assistant Examiner* — Thomas W Greig
(74) *Attorney, Agent, or Firm* — NGUYEN TARBET IP LAW

(57)        ABSTRACT

A portable automated life-saving system, comprising one or more sensors utilized for collecting data related to a patient's current medical condition and to transmit the collected data to a main computer; a main computer adapted with suitable hardware and software to process data, received from the one or more sensors, with respect to predefined medical conditions and corresponding life-saving treatment protocols, thereby to determine an initial life-saving treatment protocol to be delivered to the patient, and accordingly to operate a main controller configured to activates corresponding life-saving devices; a main controller adapted to be operated by the main computer, for controllably activating fastening means, and for controllably activating one or more life-saving devices for delivering life-saving treatment to the (Continued)

patient; two or more fastening means, controllably activated by the main controller for obtaining a firm attachment of the automated life-saving system to a patient; one or more life-saving devices controllably activated by the main controller for delivering life-saving treatment to the patient; one or more batteries. The portable automated life-saving system continuously monitors the evolving medical condition of a patient, and correspondingly adapts the given treatment, namely, the operation of the one or more life-saving devices.

20 Claims, 19 Drawing Sheets

(52) U.S. Cl.
CPC ................ *A61H 2201/0157* (2013.01); *A61H 2201/1621* (2013.01); *A61H 2201/5007* (2013.01); *A61H 2201/5097* (2013.01)

(56) References Cited

U.S. PATENT DOCUMENTS

| | | | |
|---|---|---|---|
| 2003/0212311 A1 | 11/2003 | Nova et al. | |
| 2004/0230140 A1* | 11/2004 | Steen ................... | A61M 16/024 |
| | | | 601/41 |
| 2006/0047228 A1* | 3/2006 | Petelenz .............. | A61H 31/007 |
| | | | 601/44 |
| 2009/0069726 A1 | 3/2009 | Sherman et al. | |
| 2014/0155792 A1 | 6/2014 | Karve et al. | |
| 2015/0057580 A1* | 2/2015 | Illindala ............... | A61H 31/006 |
| | | | 601/41 |
| 2015/0182160 A1 | 7/2015 | Kim et al. | |
| 2015/0231026 A1 | 8/2015 | Lurie | |
| 2016/0095765 A1* | 4/2016 | Ehrstedt ............... | A61H 31/008 |
| | | | 128/869 |
| 2016/0213560 A1 | 7/2016 | Sturdivant | |
| 2016/0249814 A1 | 9/2016 | Salerno | |
| 2017/0281464 A1* | 10/2017 | Hadizadeh .......... | A61N 1/3993 |
| 2018/0221676 A1 | 8/2018 | Patel et al. | |
| 2019/0008720 A1* | 1/2019 | Joshi ...................... | A61G 7/015 |
| 2019/0029920 A1* | 1/2019 | Kostic .................... | A61G 1/048 |
| 2019/0274920 A1* | 9/2019 | Williams ................ | A61H 1/00 |

FOREIGN PATENT DOCUMENTS

| | | | |
|---|---|---|---|
| CN | 104486989 A | 4/2015 | |
| CN | 106999043 A | 8/2017 | |
| CN | 107280946 A | 10/2017 | |
| EP | 3308763 B1 | 6/2023 | |
| JP | 2017501518 A | 1/2017 | |
| JP | 2018-45468 A | 3/2018 | |
| JP | 2018-530413 A | 10/2018 | |
| RU | 2556572 C2 | 7/2015 | |

OTHER PUBLICATIONS

Muto et al., "Digital Healthcare (Easy-to-Learn Advanced Science Series 5)", Released on Feb. 19, 2020, 5 pages.

\* cited by examiner

500

131

500

131

500

132

1201

1201a

1201

1203

1204

1202

1301

1302

PORTABLE AUTOMATED LIFE-SAVING SYSTEM WITH DYNAMIC ADAPTATION

FIELD OF THE INVENTION

The present invention relates to the field of life-saving appliances. More particularly, the present invention is a portable automated life-saving system, for the performance of a full life-saving treatment adapted to varying patient's condition, without requiring the presence of medical personnel.

BACKGROUND OF THE INVENTION

The number one death factor in the U.S. is due to cardiac failure. If such a cardiac failure is not treated within 4-6 minutes, the brain suffers from irreversible damage due to lack of receiving oxygen. Since most cardiac failures occur before a paramedic reaches the patient (for whom it takes more than 10 minutes to reach the patient), the patient's chances to survive are very low.

Cardiac failures can be a heart attack, a cardiac arrest and cardiac rate irregularities. In some cases, applying an electric shock to the heart with a defibrillator can improve the patient's condition, but in all cases, cardiac compression and continuous breathing are required until the patient is brought back to normal condition.

Conventional CPR systems usually used in the hospitals for treating heart events are large and cumbersome and also require the presence of professionals in the treatment area. Heart compression, for example, requires the intervention of a physician or a paramedic. In most cases, the physician/paramedic who provides the heart compression becomes tired quickly and a second professional person is needed to replace him. Frequently the physician/paramedic does not have the immediate information on the heart condition at the time of resuscitation, and therefore, he is unable to perform the rhythm compression specifically required for the patient.

When a person has a heart failure, there is a need to resuscitate and perform a heart artificial respiration and cardiac compression while resuscitating, to continue the blood flow to the brain in order to prevent brain damage and to keep the patient breathing (a heart malfunction can cause breathing arrest).

A cardiac failure can happen for several reasons, such as:
1. Irregular heart rate—in this case, a defibrillator that provides electrical pulses is used to restore heart rate while massaging the heart.
2. Myocardial infarction or obstruction in the blood vessels leading to and from the heart—in this case, it is very important to perform a cardiac compression at a specific rate and force corresponding to the specific condition.

Conventional resuscitation and cardiac compression systems are large, cumbersome, heavy, and are operated manually or semi-manually (not fully automatic) and require a skilled team of doctors, nurses, or paramedics to operate them.

Existing CPR systems usually perform cardiac compression at a constant rate and magnitude, which is not always good for the changing condition of the patient. When there is a positive response to the cardiac compression the magnitude and rate of the cardiac compression should be reduced. Whereas, when there is no improvement or even deterioration, the intensity and rate of the cardiac compression should be increased, in order to keep the blood flowing to the brain and prevent brain damage.

It is therefore an object of the present invention to provide a portable automated life-saving system, for performing full life-saving treatment to a patient having a cardiac arrest.

It is another object of the present invention to provide a portable automated life-saving system, for performing a full life-saving treatment, similar to the systems available in hospital care, for a long time until a professional medical intervention is accessible.

It is yet another object of the present invention to provide a portable automated life-saving system with computerized adaptation, for automatically performing full life-saving treatment for varying patient's conditions.

It is a further object of the present invention to provide a portable automated life-saving system, which does not require a skilled operator, adapted to automatically performing full life saving treatment to a patient before the arrival of a paramedic/physician.

Other objects and advantages of the invention are described in detail in the following sections.

SUMMARY OF THE INVENTION

A portable automated life-saving system, comprising:
a) one or more sensors utilized for collecting data related to a patient's current medical condition and to transmit the collected data to a main computer;
b) a main computer adapted with suitable hardware and software to process data, received from the one or more sensors, with respect to predefined medical conditions and corresponding life-saving treatment protocols, thereby to determine an initial life-saving treatment protocol to be delivered to the patient, and accordingly to operate a main controller configured to activates corresponding life-saving devices;
c) a main controller adapted to be operated by the main computer, for controllably activating fastening means, and for controllably activating one or more life-saving devices for delivering life-saving treatment to the patient;
d) two or more fastening means, controllably activated by the main controller for obtaining a firm attachment of the automated life-saving system to a patient;
e) one or more life-saving devices controllably activated by the main controller for delivering life-saving treatment to the patient; and
f) one or more batteries,
wherein the portable automated life-saving system continuously monitors the evolving medical condition of a patient, and correspondingly adapts the given treatment, namely, the operation of the one or more life-saving devices.

The system may further comprise a database related to the patient's medical history, for enabling more accurate detection of the patient's current medical condition.

The one or more sensors may be selected from the group consisting of: ECG sensors, blood oxygen saturation sensors, blood pressure sensors, Glucose blood levels sensors, or any combination thereof.

The one or more life-saving devices may be selected from the group consisting of: a chest compression device, defibrillator, a breathing assistance device, an external pacemaker, or any combination thereof.

The main controller controllably activates the life-saving devices by control signals selected from the group consisting of: electrical signals, pneumatic signals, hydraulic signals, or any combination thereof.

The two or more fastening means may comprise at least two grasping arms adapted to laterally grasp underneath a laying patient's body.

The two or more fastening means may comprise one or more inflatable pads, being inflated by pressurized means selected from the group consisting of: pressurized gas container, pneumatic inflation means, hydraulic inflation means, or any combination thereof.

The system may further comprise alerting means selected from the group consisting of: audial warning, visual warning, or any combination thereof.

The alerting means may be utilized for guiding a treating person as of required operations, as well as of clearance required before the system discharges an electric shock to a patient.

The system may further comprise a battery status indication means indicating regarding the battery's charging level.

The one or more sensors may be connected to communicate with the system by connection means selected from the group consisting of: wired connection, Bluetooth connection, Wifi connection, or any combination thereof.

The system may further comprise connection ports selected from the group consisting of: USB port, memory card reader port, Ethernet port, or any combination thereof.

The system may further comprise a memory card reader.

The system may further comprise an Ethernet connection port.

The system may further comprise remote communication means for contacting medical assistance and other predetermined contacts.

The remote communication means may be selected from the group consisting of: Cellular communication device, Wifi communication device, or any combination thereof.

The ECG sensors may be integrated with the two or more fastening means.

One defibrillator electrode may contact the patient's chest, while a second defibrillator electrode may contact the patient's back, thus enabling the generation of electric shock from opposed sides of the heart.

The system may further comprise:

a) a mobile phone application for allowing remote exchange of data and control signals with external servers;

b) a blood pressure cuff for allowing patient's blood pressure measurements; and c) an external remote control for remote system operation, changing telephone numbers and receiving faults.

The adjustment mechanism comprises lateral rails and longitudinal rods for adjusting the displacement of the fastening means.

The main computer is adapted to continuously record the ongoing medical condition of a patient.

The system may further comprise a self-test operation enabling a user to test his condition.

The system may further comprise a wall cabinet for storage when the system is not in use, wherein the wall cabinet is adapted with gel sockets correspondingly positioned for maintaining ECG leads of the system lubricated with a gel layer.

At least one of the one or more sensors may be embedded within a wearable bracelet.

A wearable monitoring bracelet, comprising at least one ECG sensor, pulse sensor, and communication means for communicating with corresponding emergency services when detecting that the wearing person is experiencing an emergency condition.

A monitoring and alerting system, comprising one or more wearable monitoring bracelets adapted to communicate with a wall mounted control box, which is configured to alert to an emergency service, and to sound audial alert upon detecting a medical emergency experienced by one or more persons wearing the one or more wearable monitoring bracelets.

BRIEF DESCRIPTION OF THE DRAWINGS

The above and other characteristics and advantages of the invention will be better understood through the following illustrative and non-limitative detailed description of preferred embodiments thereof, with reference to the appended drawings, wherein.

DETAILED DESCRIPTION OF THE PRESENT INVENTION

The present invention relates to a portable automated life-saving system, which is capable of optimally detect a patient's emergency medical condition, and accordingly to perform a life-saving treatment, such as a Cardio Pulmonary Resuscitation (CPR) by artificial respiration and cardiac compression devices, while continuously monitoring the patient's vital signs (e.g., Electro Cardio Gram (ECG) signals, blood pressure, oxygen level, heart pulses, and glucose level), and adapting the delivered treatment protocol to the patient's evolving medical condition. The proposed system is compact, lightweight, adapted to be worn on a patient's body of any body size and shape, and can be simply activated by a regular person without requiring any medical skills.

The proposed life-saving system is configured to continuously monitor and analyze the patient's current medical condition based on data received from several sensors, and with respect to pre-known medical conditions and corresponding treatment protocols. The proposed system continuously adapts the delivered treatment (e.g., performance parameters of the CPR devices) to the responsiveness of the patient, namely, to the evolving patient's medical condition (e.g., reduce the intensity of chest compressions whereas a target blood pressure is obtained). The monitored data and delivered treatment protocol are saved constantly, and can be retrieved by the medical staff for treatment continuity and future use.

Figure 1A:
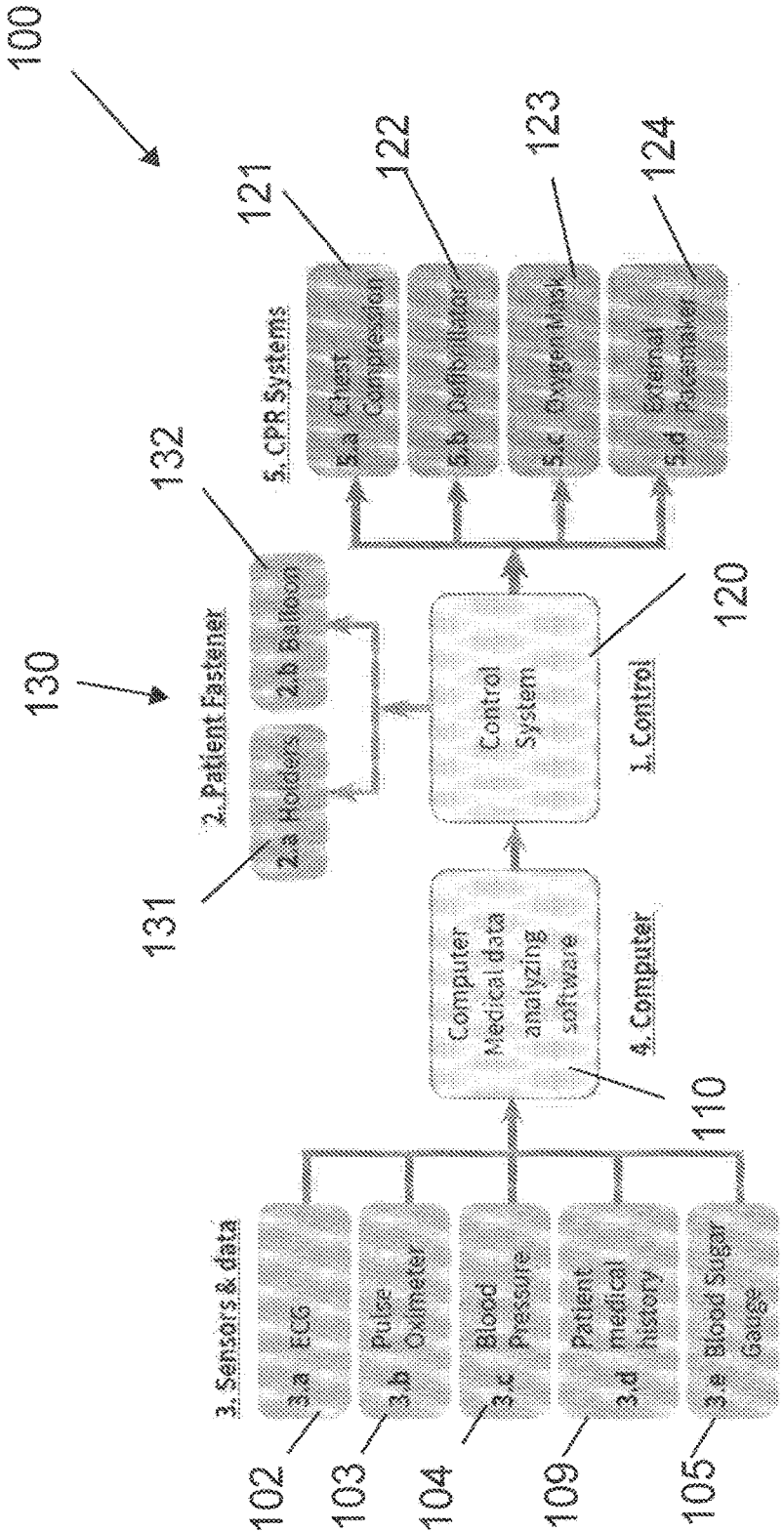
FIG. 1A-1C shows a block diagram of an exemplary configuration of a portable automated life-saving system, according to an embodiment of the present invention.
Figure 1B:
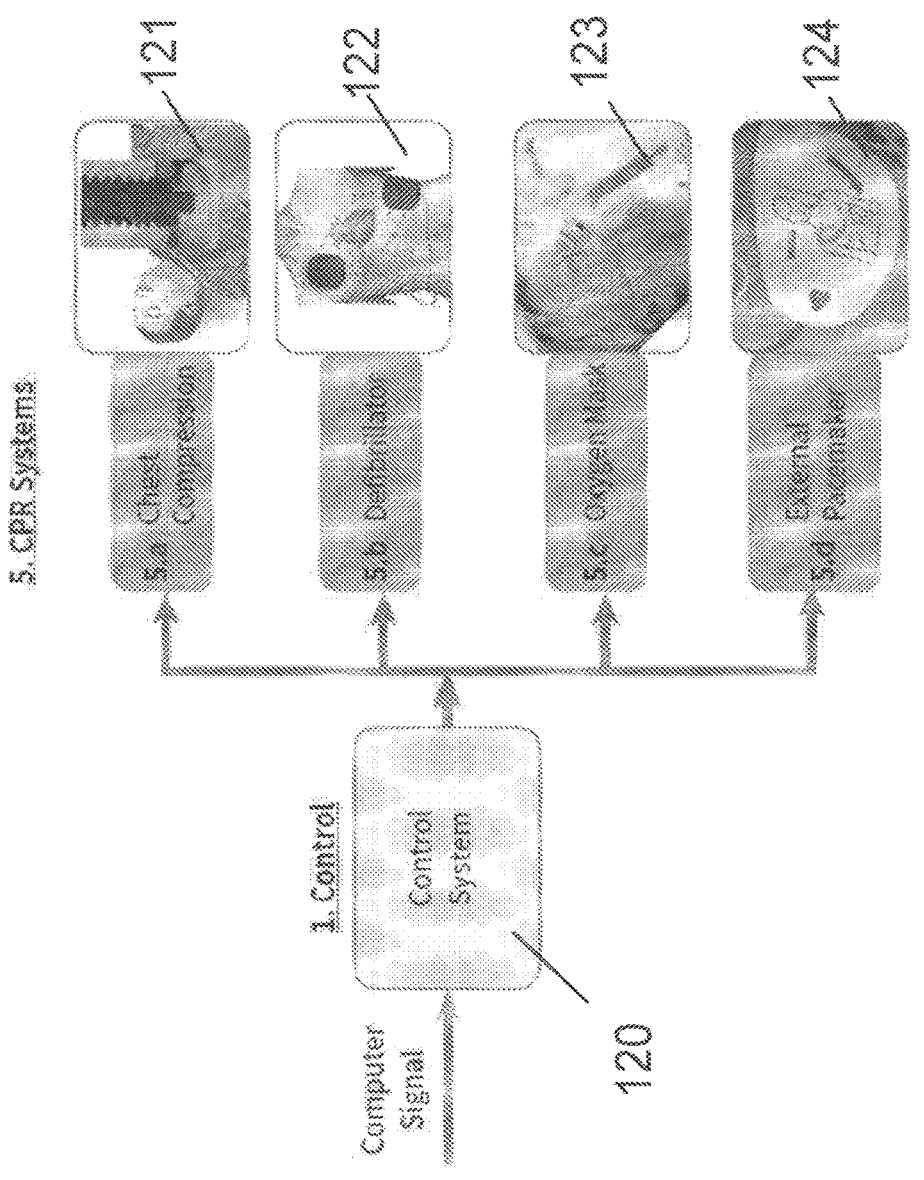
Figure 1C:
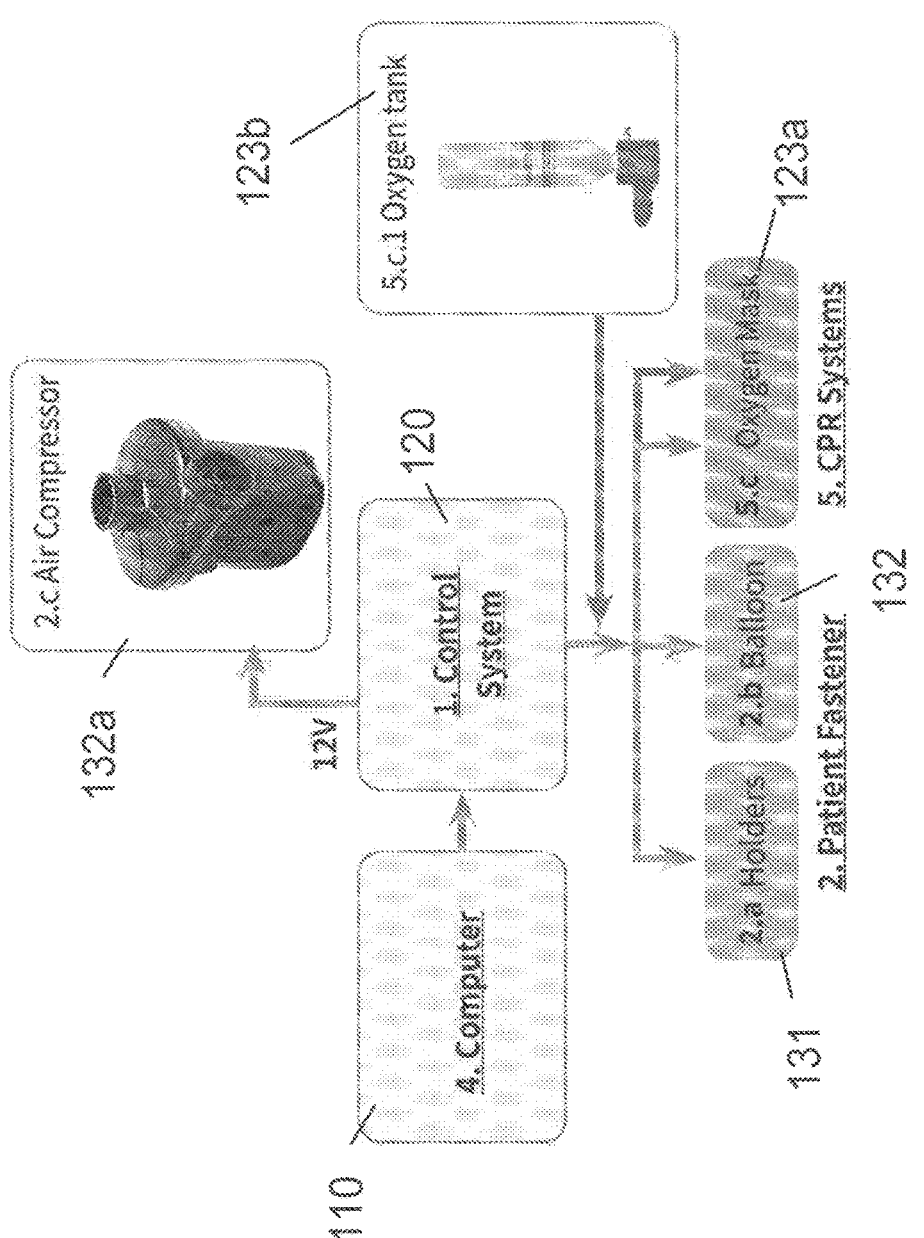

FIG. 1A-1C shows a block diagram of an exemplary configuration of a portable automated life-saving system 100, according to an embodiment of the present invention. System 100 comprises a main computer 110 which is configured to detect a patient's current medical condition, determine a corresponding life-saving treatment, and to deliver the determined treatment by operating a main controller 120 which is adapted to control suitable life-saving devices (further explained in the following figures herein), by electric or by electromechanical means such as air pressure pulses.

Computer 110 comprises suitable hardware (e.g., processor, memory, storage and communication means) to run a dedicated medical software, which is configured to process data received by computer 110 from a plurality of sensors, and a database related to the patient's medical history, and a database of multiple predefined medical conditions and corresponding life-saving treatment protocols, according to which computer 110 characterizes the patient's current medical condition and determines an initial life-saving treatment protocol to be delivered to the patient, through controller 120.

According to an embodiment of the present invention, the following sensors are utilized for monitoring and characterizing the patient's medical condition:

a. An ECG module 102 which provides data for assessing the patient's heart functioning. Computer 110 is configured to receive the ECG signals data and convert it into digital data using several parameters that express the patient's heart condition.

b. A pulse oximeter 103 which continuously measures the pulse and the instant oxygen saturation values in the patient's blood. Pulse oximeters are of critical importance in emergency medicine providing useful information related to patients with respiratory or cardiac problems.

c. Blood pressure gauge 104 measures the blood pressure which is also indicative of cardiac problems.

d. Blood sugar gauge 105 (e.g., non-invasive blood sugar sensors based on ultrasonic/electromagnetic/light/heat waves propagation analysis, to infer the blood sugar level) to measure blood sugar level to prevent unnecessary activation of the system in cases of decline or increase in blood sugar that are manifested as cardiac problems.

Of course, the proposed system is not limited for utilizing the abovementioned sensors 102-105 or other sensors currently known in the art, and can be readily adapted to receive and process data from futurity developed sensors as corresponding technologies are continuously developing.

Computer 110 further utilizes medical database 109 which stores data related to the patient's medical history (i.e., past medical conditions, given treatments and patient's response to the treatments). Medical database 109 is stored locally by computer 110 (e.g., an internal electronic media integrated with computer 110, an electronic storage device in near range wireless communication with computer 110, an external device, such as a patient's personal memory device, being physically connected to a corresponding port of system 100, or a combination thereof), or remotely by a remote server(s) with which computer 110 communicates by utilizing suitable communication means (e.g., a Wifi device, a cellular communication device, etc.), thereby computer 110 can access a remote database, and/or update its local database.

Utilizing a patient's medical history can be critical for correctly analyzing a set of monitored vital signs which can be interpreted into different conditions, for example, whereas a patient displays low oxygen saturation and fast shallow breaths, and therefore being treated with oxygen, the knowledge that the specific patient is a chronic obstructive pulmonary disease (COPD) patient can make a critical difference as to the administered oxygen levels.

Medical database 109 further stores data related to medical conditions, and corresponding treatment protocols, which are not related to a specific patient, where the inclusive medical data stored by database 109 is initially utilized by computer 110 to optimally determine a treatment protocol by comparing the patient's current condition characterized by the data received from sensors 102-105, to general pre-known medical conditions as well as to the specific patient's medical history, thus enabling more accurate detection of the patient's current medical condition.

According to an embodiment of the present invention, system 100 comprises the following treatment devices (also illustrated in FIG. 1B) controlled by controller 120:

a. A chest compression device 121 adapted to deliver chest compressions at a rate (i.e., compressions per minute), amplitude (e.g., which may vary from 5 kg to 25 kg) and stroke (e.g., up to 5 cm), as determined by computer 110, in order to obtain a target blood circulation.

b. A defibrillator 122 for delivering an electrical shock at amplitude and timing determined by computer 110 (e.g., whereas cardiac pace disorder conditioned is detected).

c. A breathing assistance device 123 (illustrated to details in FIG. 1C) adapted to supply ambient air with 21% oxygen through mask 123a, or whereas computer 110 determines that a patient should be supplied with enriched air with higher oxygen levels, controller 120 controls the valve of an oxygen tank 123b for enriching the supplied air through mask 123a.

d. An external pacemaker 124 adapted to provides low currents to the heart at a controlled rate (e.g., a frequency of 60-80 times per minute).

Also shown in FIG. 1C are fastening means 130 (further illustrated in the following FIGS. 2A-2B and 9) comprising grasping arms 131, which are controlled by controller 120, per fastening commands sent by computer 110. Fastening means 130 are required for obtaining a firm attachment of system 100 to a patient as well as sufficient contact between the electrical monitoring sensors (e.g., ECG 102) and treatment devices (e.g., defibrillator 122) and the patients, to enable effective monitoring and treatment. At the first step, two grasping arms 131 (further details are in FIG. 9) that initially extend to its maximal extent (e.g., an extent suitable to confine large body-sized patients) followed by a pivotal movement to grasp below the patient's back (i.e., presuming system 100 is initially positioned on the chest of a lying patient) and to hold the system body close to the patient's chest. The elastic pads 132, fills the gap to the patient's chest and tightens the system's body to the patient's chest. According to some embodiments of the invention, a single air compressor 132*a* is controlled by controller 120 (i.e., a corresponding flow rate determined by computer 110) for providing air at relatively low capacity to oxygen mask 123*a,* which can also be enriched with oxygen provided by oxygen tank 123*b.* System 100 also comprises suitable pressure gauges (e.g., potentiometric sensors, capacitive sensors, piezoelectric sensors, etc.) deployed at the contact area with a patient's chest, or integrated with the ECG leads 211, for detecting a sufficient attachment is achieved, while avoiding excess pressure to be applied on the patient's body.

Whereas the fastening tightening operation completes, system 100 begins monitoring the patient's medical condition and delivers life-saving treatment determined by computer 110.

Figure 1D:
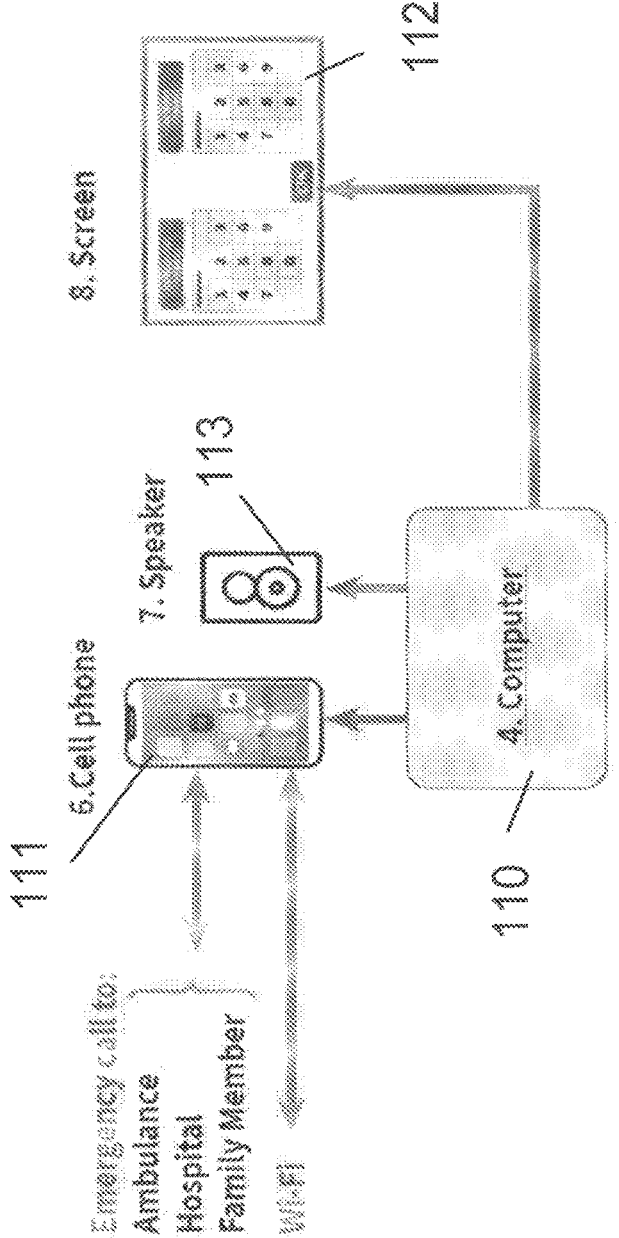
FIG. 1D shows an exemplary interfaces block diagram of the proposed system 100, according to an embodiment of the present invention.

FIG. 1D shows an exemplary interface block diagram of the proposed system 100, according to an embodiment of the present invention. Computer 110 is capable of interfacing with an adjacent mobile device (e.g., by near communication means such as Bluetooth, Wifi, etc.) such as smartphone 111, utilizing the communication and location detection means to contact and update the emergency services with the ongoing medical emergency, the patient's condition and its location, thereby suitable medical assistance can be urged to the patient and the nearest medical facility can be notified and get prepared to the patient's arrival. According to some embodiments of the invention, system 100 utilizes an internal cellular modem in lieu or in conjunction with a smartphone 111.

Also shown in FIG. 1D are display screen 112 and speaker 113 with which computer 110 interfaces for displaying and announcing informational, guiding, and warning information to the patient's surroundings. While both display 112 and speaker 113 can be integrated with system 100, the latter can be adapted with wired/wireless connection means for interfacing with external display 112 and/or speaker 113.

System Operation Steps

At the first step, the system is removed from a storage box (e.g., a carrying case and/or storage case being attached to a structure's wall) and is placed onto the patient's body (i.e., in most emergency medical cases, the patient is laying or being laid on a horizontal surface). Removing the system from the storage box triggers an alarm (e.g., sounds for a limited period of time such as 15 seconds), so as to alert people from the close vicinity to assist and/to clear the area near to the patient. At the end of the alarm, computer 110 operates smartphone 111 or an alternative integrated communication means for calling one or more predetermined phone numbers (e.g., local ambulance service, a family member, a family physician, etc.). At the next step, the treating person (i.e., an occasional bypassing person who can hold no medical skill) places the system on the chest of the patient, places the patient's hands sideways, while positioning chest compression device 121 above the center of the patient's chest bone, between the patient's ribs.

At the same time, the treating person assembles the pulse oximeter 103 on a patient's finger and activates the blood pressure gauge 104. At the next step, the treating person presses the (red) power button. In response, the system automatically performs the following operations:

1. The grasping arms 131 extend out of the system body and in turn grasps the patient's back and the system is pressed against the chest.
2 The elastic pads 132 (detailed in FIG. 11) located at the bottom of system 800 (as illustrated in FIG. 8*b*) generate an adjustable contact between system 800 and the patient's chest, thus enabling the adaption of system 800 to variable body patterns and sizes.

This arrangement compensates for the various forms of patients' chest. ECG 102 pads and defibrillator pads of defibrillator 122 are integrated with one (or two) of the elastic pads 132 being pressed against the patient's body. Automatic pressing brings the sensors to the desired location.

3. Computer 110 triggers sensors 102-105 to begin obtaining the patient's medical condition. The sensors can be operated continuously (e.g., ECG 102, pulse oximeter 103, blood pressure gauge 104, and glucose meter) or intermittently (e.g., blood pressure gauge 105).
4. The data is streamed to the main computer 110 which characterizes the patient's medical condition and compares it with pre-known conditions stored in database 109 utilizing medical algorithms which also considers the patient's medical history, if available, to identify the most similar pre-known conditions and the corresponding treatment protocol.
6. Computer 110 operates controller 120 to controllably activate one or more life-saving devices (i.e., at performance levels defined by the treatment protocol determined by computer 110).

According to some embodiments of the invention, the removal of system 100 of its storage triggers computer 110 to begin streaming guiding instructions through speaker 113, guiding the treating person as of how to prepare the patient (e.g., "lay the patient on a solid surface", "place the patient's hands sideways", etc.) and with the placement of system 100 with respect to the patient's chest.

Figure 2A:
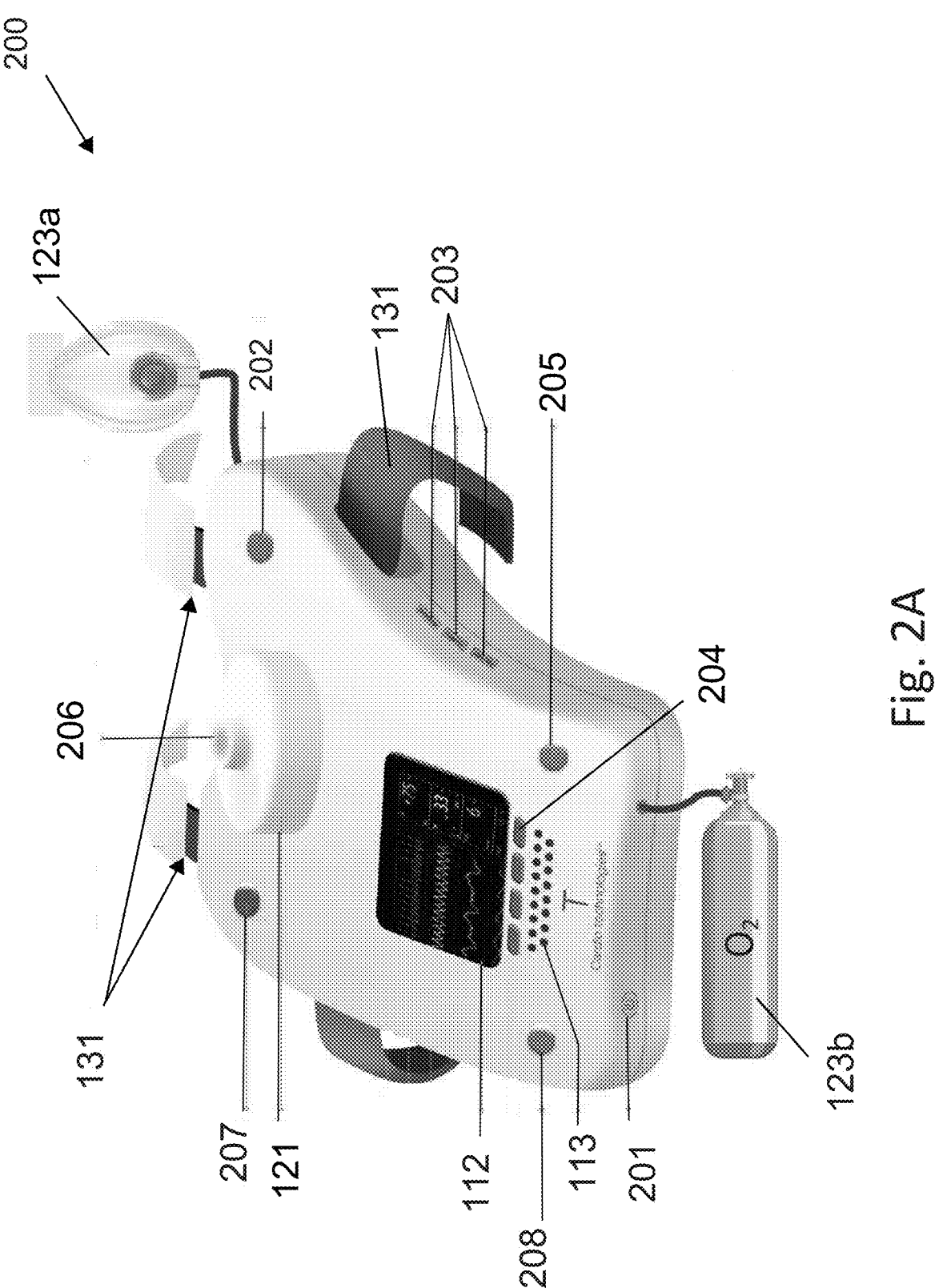
FIG. 2A shows a front view of a portable automated life-saving system 200, according to an embodiment of the invention.

FIG. 2A shows a front view of a portable automated life-saving system 200, according to an embodiment of the invention. The body of system 200 is attached to the shoulders of the patient by two grasping arms 131 (e.g. clasps), while system 200 is positioned on the patient's chest with the neck of the patient in the center between the two clasps 131 and additional grasping arms 131 fasten system 200 to the patient's chest at the back and waists of the patient.

System 200 further comprises a display screen 112 (e.g., a touch screen) which shows the diagnosis of the current event, a power On/Off button 201, a Built-In Test (BIT) button 202 for self-testing the proper operation of system 200, USB sockets 203 for connecting various accessories to system 200 (e.g., a charging cable to recharge the battery of system 200), operational keypad 204, battery capacity status check button 205, an electric alarm light 206 for providing a warning to the surrounding people regarding actual or impending electric shock, a speaker 113 for audial warnings and guidance and instructions for the operator of the system, a chest compression device 121 (top cover of which is shown in FIG. 2A) and an oxygen mask 123*a,* which is worn on the patient face to provide breathing assistance with oxygen enriched air, whenever necessary.

USB sockets 203 may also be used to connect an external computer or mobile device to system 200, thereby entering new data from a computer or a mobile phone, for example, changing a telephone device, and retrieving the measured data for use by professional medical staff doctor, etc. System 200 also comprises a MICRO SD socket (not shown) for connecting an external memory drive, and emergency stop button 207 to allow the operator to manually stop its operation at any time.

System 200 further comprises a self-test button 208 for allowing any patient (or user) to independently test his condition such as when experiencing chest pain, tightness or any other distress (i.e., of course, computer 110 is configured to disable self-test button 208 from initiating functions which are not supposed to be initiated independently by a patient, such as a chest compression device 121, defibrillator 122, or breathing assistance device 123). In such an event, the user lays the system on his chest, activated by a self-test button, and computer 110 initiates the monitoring means (e.g., sensors 102-105), displaying the monitored information on the display screen 112. The self-test process will end automatically after completing reading the sensors, arms 131 are released and fold back to their stored position. System 200 is configured to submit the self-test results to a predetermined remote computing device, such as a physician's computer/mobile device, and if an actual emergency condition is detected system 200 communicates the results to predetermined emergency services center urging medical assistance for the patient, and sending the geographic location of the patient. The geographic location may be detected by a GPS unit embedded in system 200, or with a wearable device worn by the patient and in communication with system 200.

For example, in the self-test mode, the proposed system may also be adapted to analyze the results of a blood test that the user performs, namely, to detect a certain level of enzymes (e.g., Troponin) that may be considered as biologic markers indicating a person recently experienced a cardiac event.

Figure 2B:
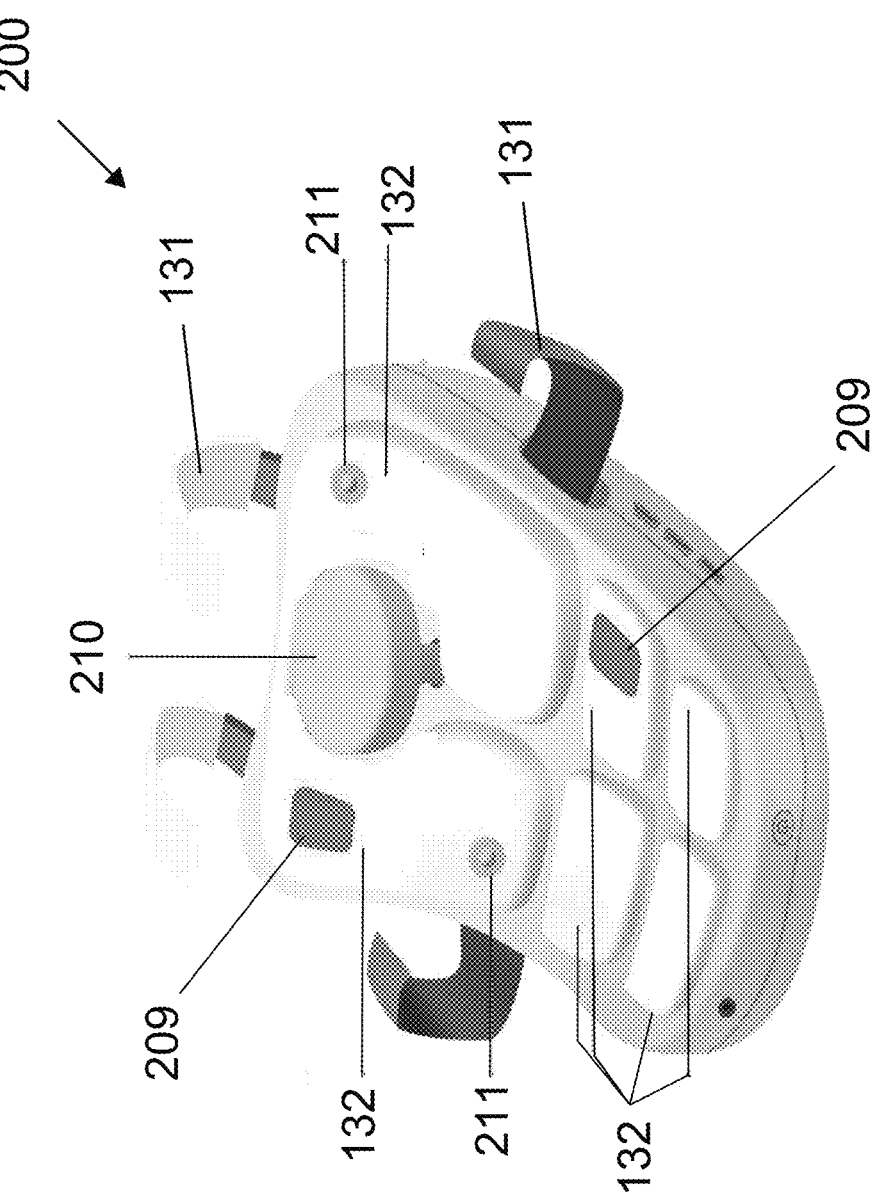
FIG. 2B is a bottom view of the system of FIG. 2A.

FIG. 2B is a bottom view of system 200, showing defibrillator pads 209 of defibrillator 122 (of FIG. 1A) adapted to apply an electric shock, chest compression piston 210 of chest compressions device 124 (of FIG. 1A), elastic pads 132 (detailed in FIG. 11) which are utilized for obtaining good attachment and contact between system 200 and the patient's body, and ECG sensing leads 211 of ECG sensors 102 for measuring the ECG signal from the patient's heart continuously. Defibrillator pads 209 also serve an external pacemaker 124 (of FIG. 1A) for providing low currents to the heart at a predetermined frequency via these pads 209.

An alternative option for implementing pads 132 is inflatable pads which can be filled by an air compressor.

Figure 3:
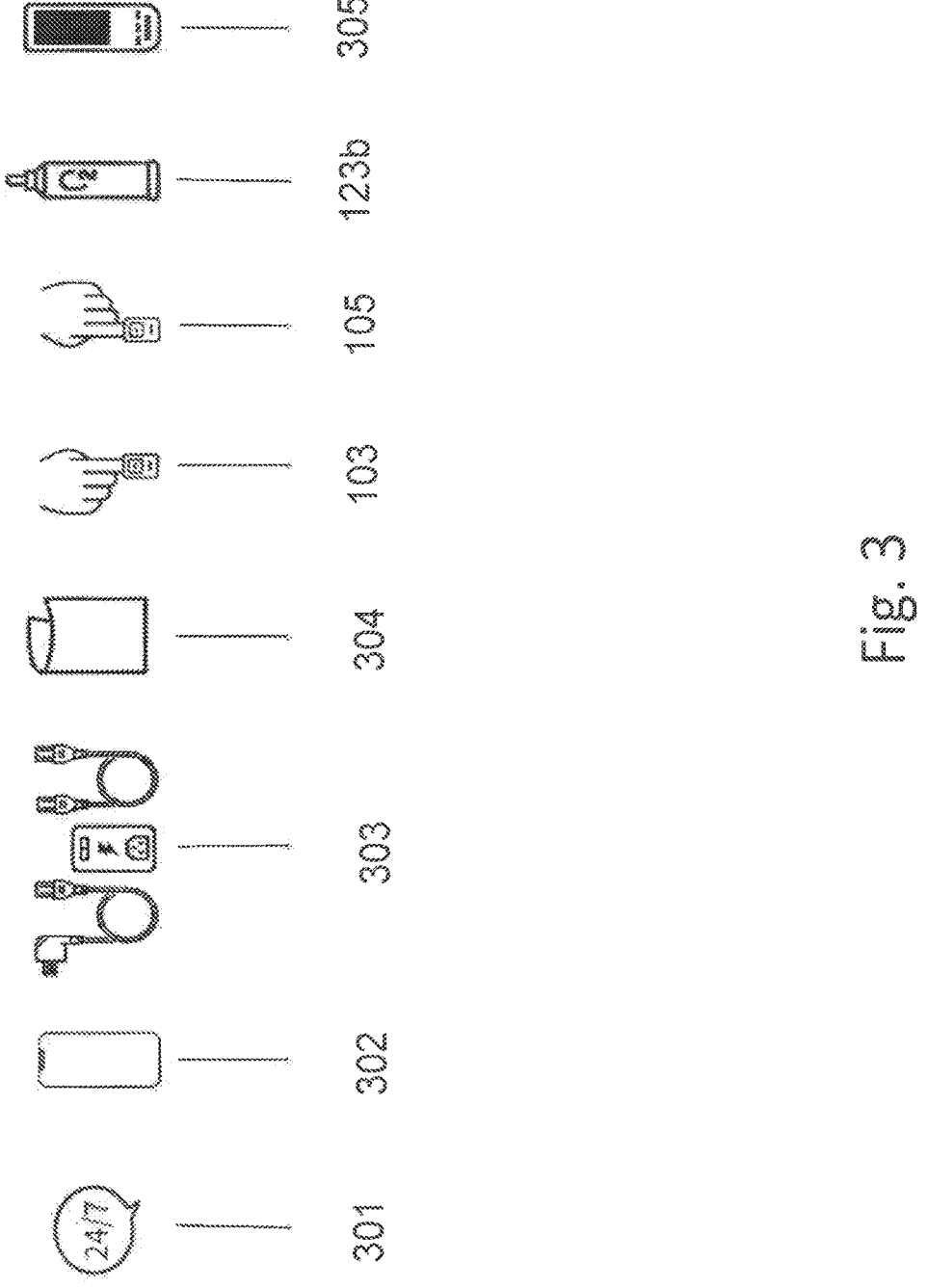
FIG. 3 schematically illustrates additional accessories, according to an embodiment of the invention.

FIG. 3 schematically illustrates additional accessories and services which can be provided with system 200, consisting of a 24-hour control center 301 which receives calls and data from each operating device and provides help and guidance to the user via speaker 113 and display 112, a mobile phone application 302 for allowing a remote exchange of data and control signals with external servers, power appliance and cables 303 for recharging the battery and providing power to the device as long as being connected, blood pressure cuff 304 for allowing patient's blood pressure measurements, blood oxygen meter 103 to be mounted to the patient's fingertip for measuring the proportion of oxygenated hemoglobin in the patient's blood, blood sugar gauge 105, an oxygen tank 123b for providing oxygen to the oxygen mask 123a and an external remote control 305 for remote system operation, such as updating significant telephone numbers (i.e., contacted by the proposed system in emergency events) and receiving faults.

10

Figure 4:
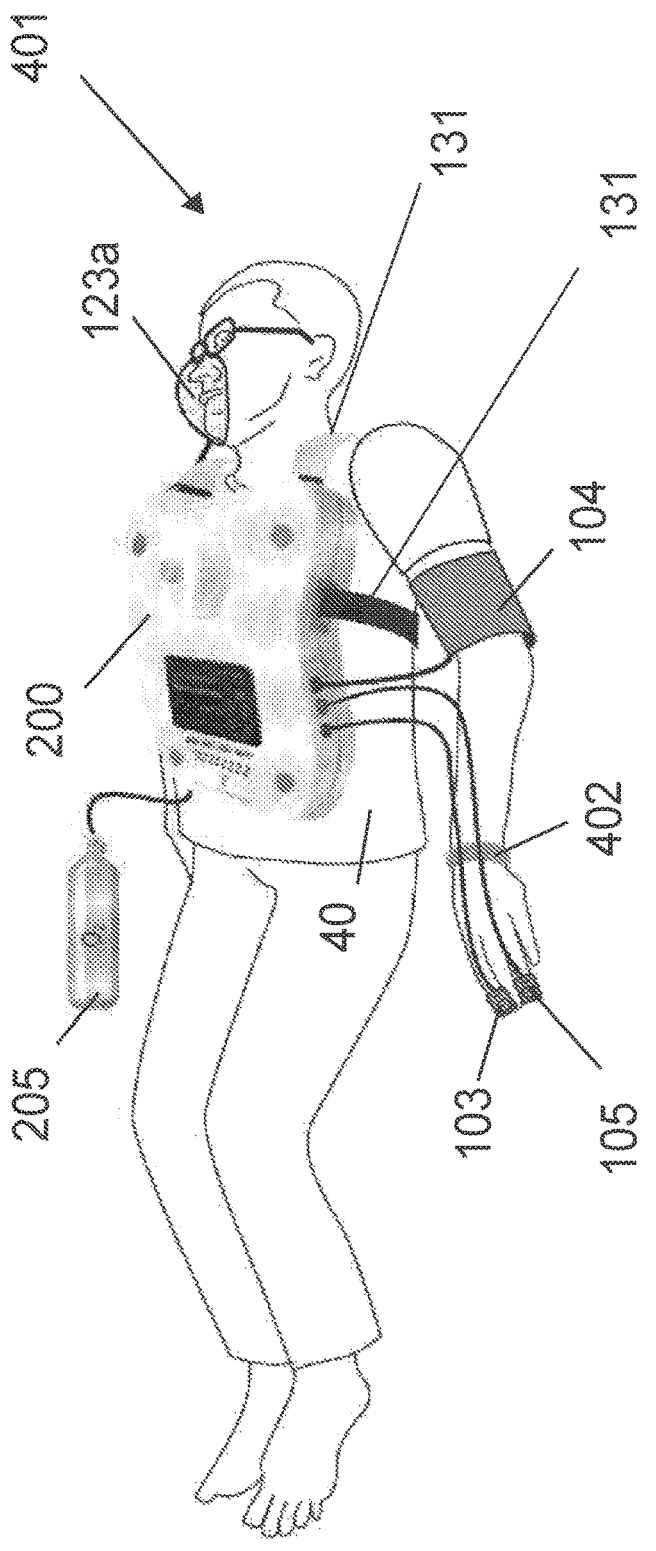
FIG. 4 is an illustration of a person wearing the system of FIGS. 2A-2B, according to an embodiment of the invention.

FIG. 4 is an illustration of a person 401 wearing system 200, according to an embodiment of the present invention. An oxygen mask 123a is worn on the person's face, the body of the system 200 is attached to the person's chest by two grasping arms 131 on the chest, and two grasping arms 131 on the shoulders, oximeter sensor 103 and glucometer 105 are attached to the person's fingers, a blood pressure gauge 104 is applied to the person's arm for continuously measuring the patient's blood pressure.

The proposed system is adapted to be in wired/wireless communication with a wearable sensor 402 in the form of a flexibly wearable bracelet, which can be worn by the user on his hand. Bracelet 402 comprises an internal sensor for sensing heart pulses, oximeter, and glucometer. An internal transmitter periodically transmits the data (i.e., to the proposed system), which is analysed to evaluate the patient condition. Upon detecting predetermined parameters, indicating cardiac distress or failure, the proposed system 100, system 200 activate all the required CPR functions and transmit a corresponding alert to corresponding medical services, along with the location of the user.

Bracelet 402 may also be adapted with further sensors: oximeter, blood pressure, ECG, and temperature, for providing additional diagnostic data to computer 110 of the proposed system. According to an embodiment of the present invention, bracelet 402 is internally adapted with oximeter 103, blood pressure sensor 104, and glucometer 105, thus eliminating the need for separately worn sensors.

Figure 5A:
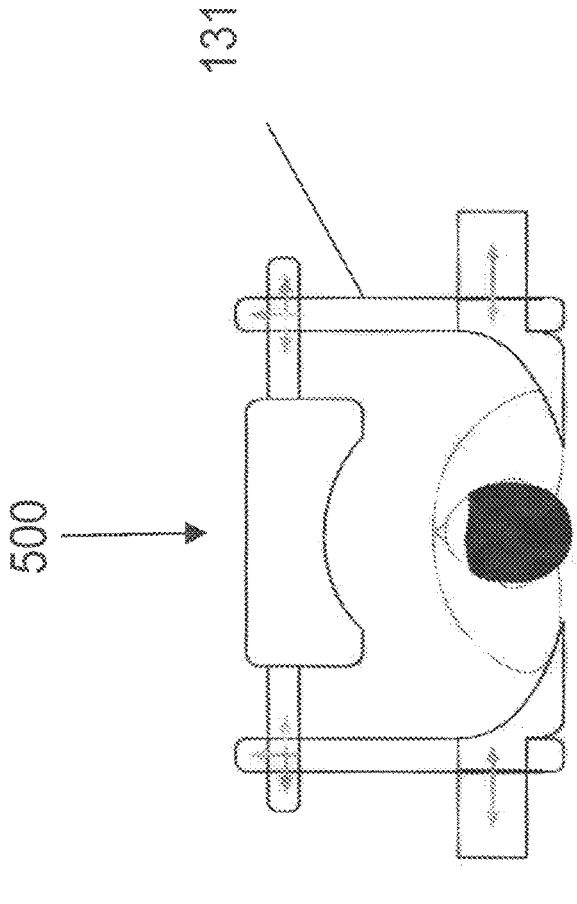
FIGS. 5A-5C illustrate the side harnessing of the proposed system to a laying person, according to an embodiment of the present invention.
Figure 5B:
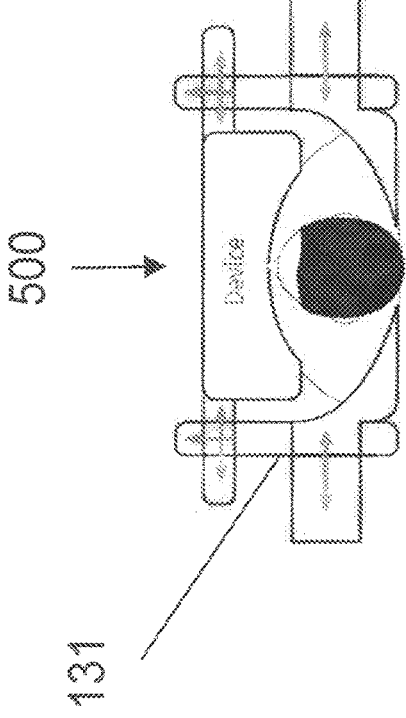
Figure 5C:
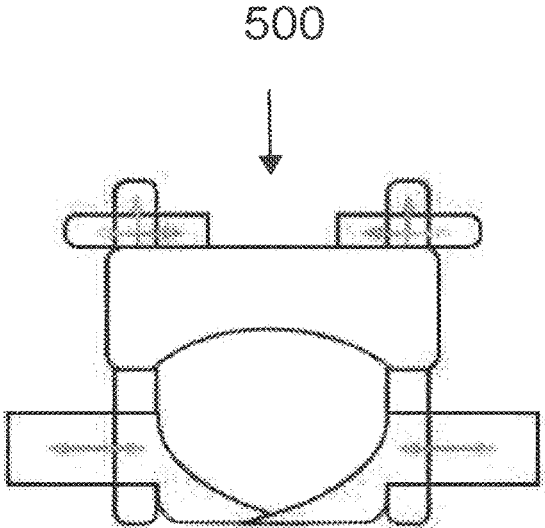

FIGS. 5A-5C illustrate the side harnessing of the proposed system to a laying person, according to an embodiment of the present invention, in which system 500 is initially being positioned onto the patient's chest, with chest compression device 121 positioned above the center of the chest, with two shoulders' grasping arms 131 being positioned onto the patient's shoulders (as illustrated in FIG. 4). The lateral two grasping arms 131 which grasps underneath the patient's waist, initially extends laterally, then fold down to a vertical state (FIG. 5A), and in turn, retract vertically (FIG. 5B) and finally retracts laterally (FIG. 5C) to a complete adaption to the patient's chest (the complete details of the holder system 800 illustrated in FIG. 9).

Of course, multiple different extension arrangements can be selected by a person skilled in the art, suitably for different sizes and shapes of the proposed system, such as lateral rails/rack and pinion arrangement and vertical pneumatic extension mechanism, or any other arrangement providing lateral and vertical extension as well as rotation of arms 131, without departing the described grasping and adaption process which provides a firm grasping without applying excess load onto the patient's body.

Figure 6:
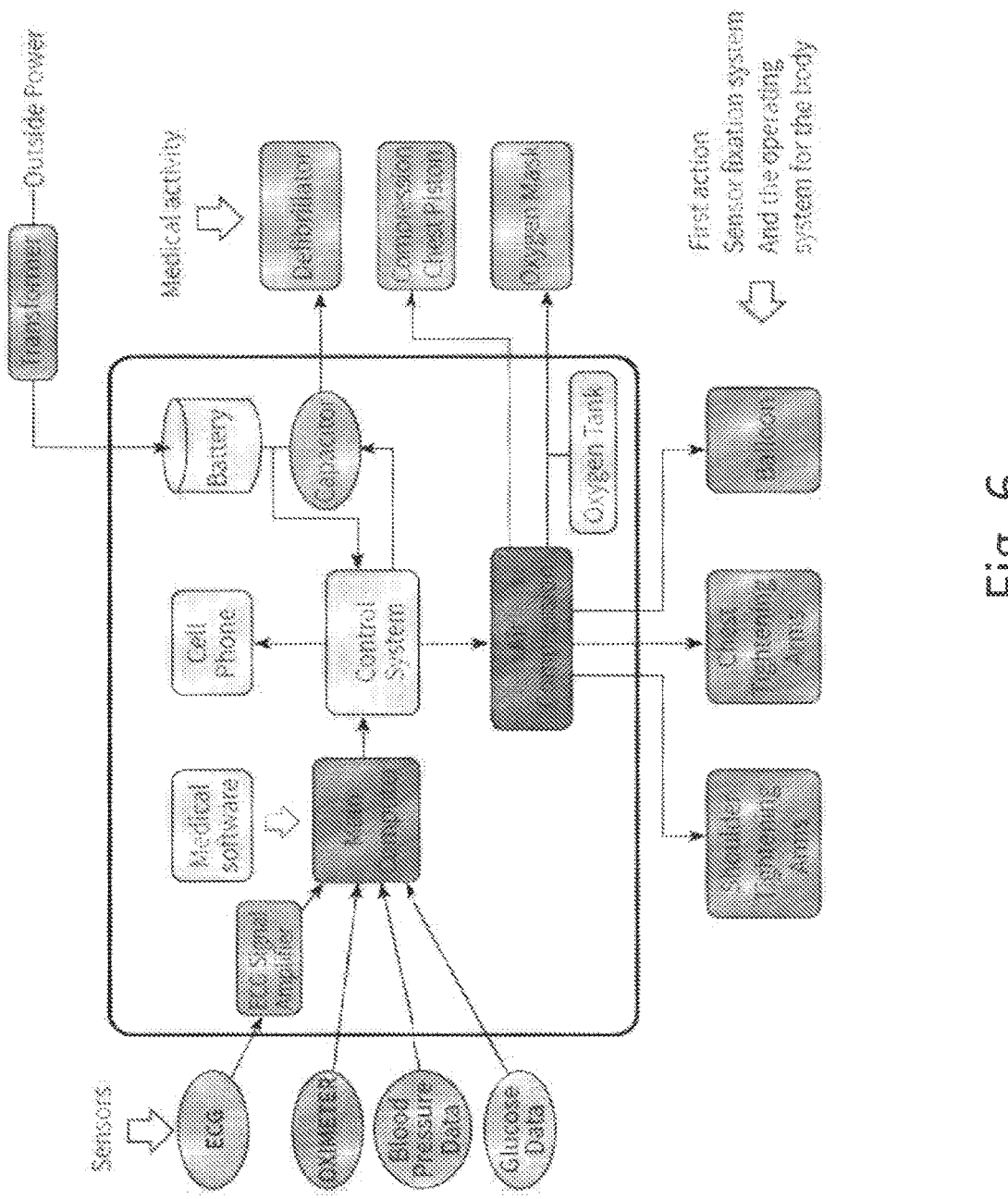
FIG. 6 illustrates an exemplary components diagram of the proposed system, according to an embodiment of the present invention.

FIG. 6 illustrates an exemplary components diagram of the proposed system, according to an embodiment of the present invention. The proposed system includes a rechargeable battery with an external power charging source, a capacitor for stabilizing the operating voltage, a control system for controlling the functional operation of the system, a cell phone for communicating with remote medical authorities, a blower and oxygen balloon for providing breathing assistance with oxygen enriched air, a defibrillator, a cardiac compression piston, an elastic pads for obtaining good attachment to the patient's body (the defibrillator pads, measuring ECG leads are attached with the elastic pads to the patient's body), a shoulder grab, chest grab and back grab, a computer with SIM card (to connect the system to Emergency Medical Center, the patient's doctor or patient family), medical software for analyzing the patient's heart condition according to the measuring sensors. The software determines the optimal treatment based on a large medical database. ECG sensors for measuring the ECG signal from the patient's heart continuously and in real-time and software that transforms the ECG signal into a digital readout, oximeter for measuring the proportion of oxygenated hemoglobin in the patient's blood (which can affect the power and rate of the cardiac compression and the enrichment of the resuscitation air with oxygen that need to be given to the patient) and blood pressure meter for measuring the blood pressure of the patient continuously and in real-time, and a sugar sensor to measure the blood glucose level.

According to the ECG signal measuring from the patient's heart continuously and in real-time, the system operator decides if there is a need to give the patient an electric shock by the defibrillator and in which power, activating an alarm, turning on and off lights and counting down display from 0 to 5 to clear the area. Then the electric shock is given to the patient by the defibrillator and the system starts to give the patient a cardiac compression by an automatic piston, while determines and monitors the heart rate of the patient. At the same time, the pacemaker starts to operate continuously.

The system may also comprise an ECG amplifier for increasing the magnitude of the ECG signals, in order to isolate them from background noise and separate them from other signals in the system before reaching the main computer.

Figure 7:
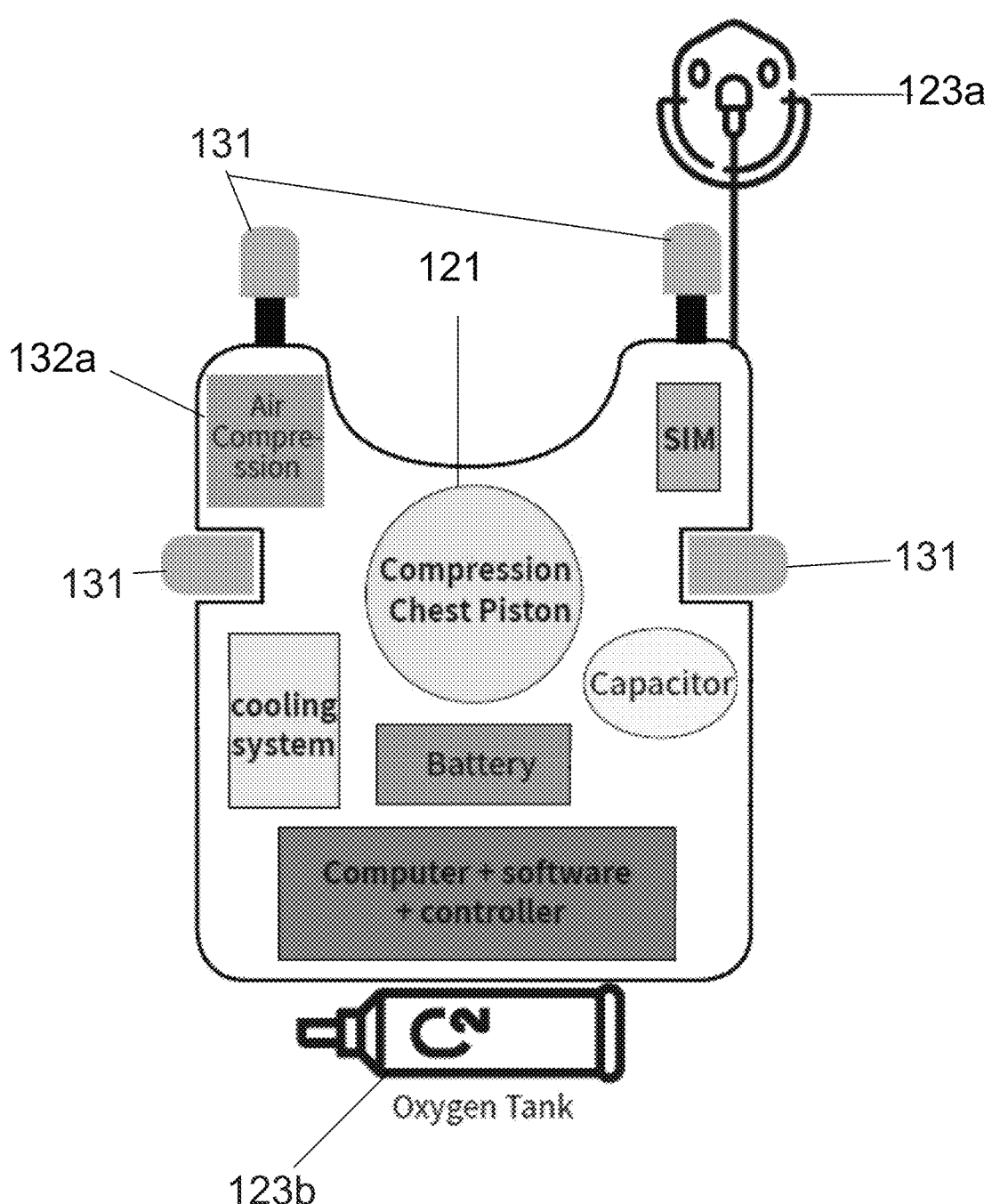
FIG. 7 is a front view illustration of the proposed system supplementary parts.

FIG. 7 is a front view illustration of the proposed system's supplementary parts: the blower, cooling system, oxygen tank and cardiac compression plunger, oxygen mask, battery, a SIM card, capacitor, electronic cards, computer, software and controller.

Figure 8A:
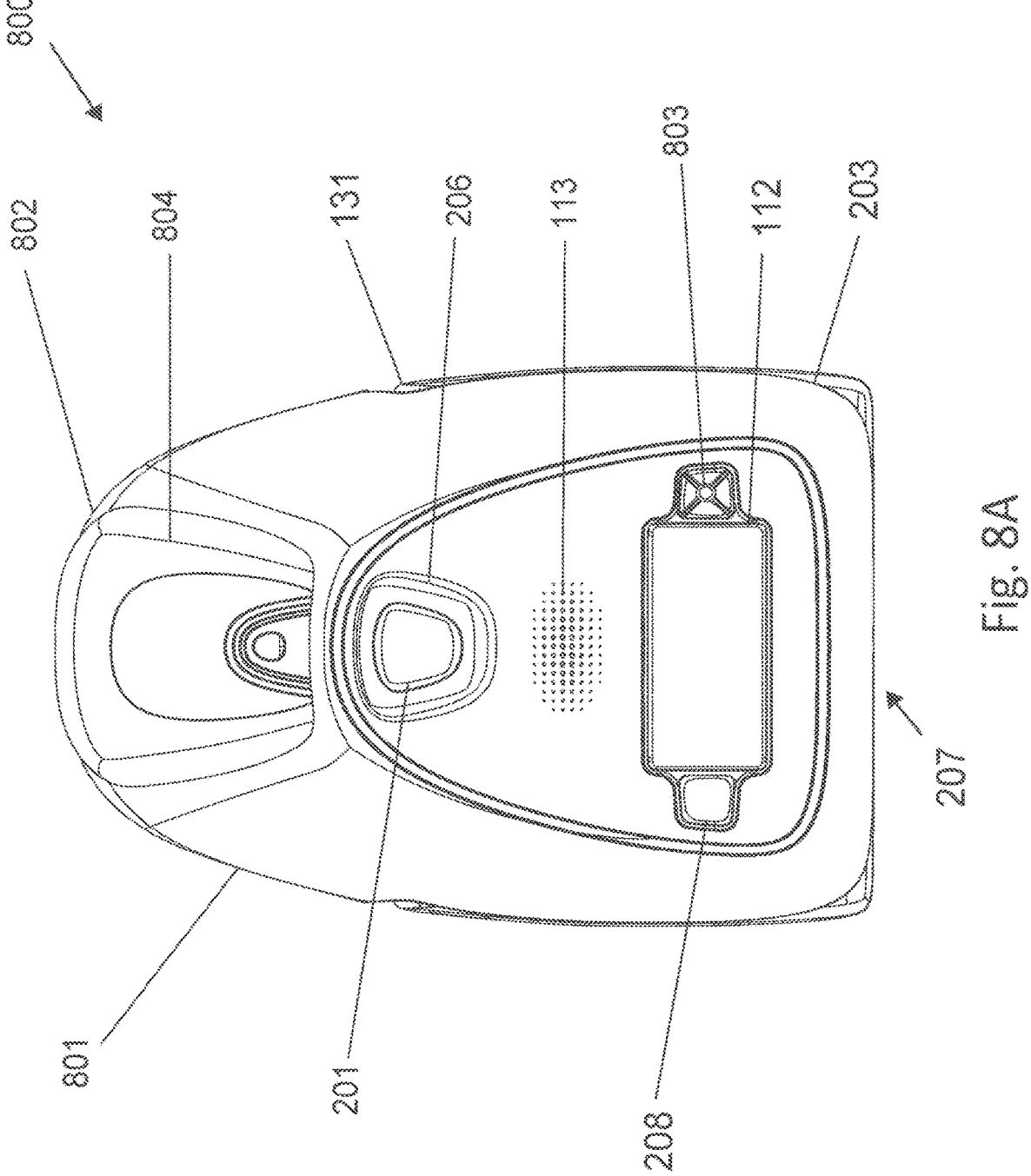
FIG. 8A schematically illustrates a top view of a portable automated life-saving system 800, according to an embodiment of the invention.
Figure 8B:
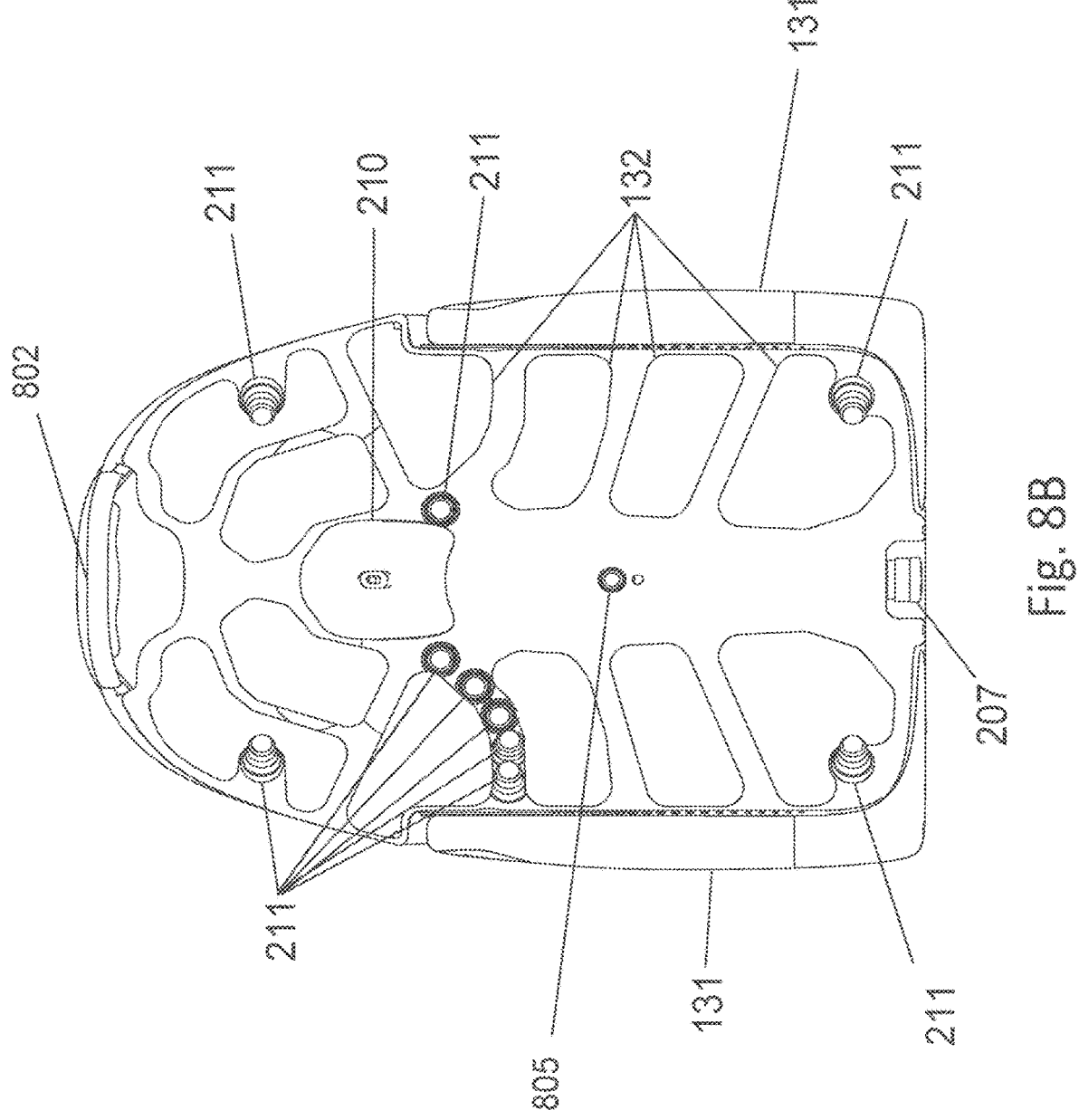
FIG. 8B schematically illustrates a bottom view of the system of FIG. 8A.

FIG. 8A schematically illustrates a top view of a portable automated life-saving system 800, according to an embodiment of the invention. System 800 comprises an ergonomically shaped enclosure 801 in which the different components are integrated such as a retractable handle 802 (in storage position, hence, not shown in FIG. 8A), a power On/Off button 201, USB sockets 203, a touch screen 112 (also illustrated in FIG. 2A), Joystick operation pad 803 (i.e., together with the touch operator of touch display 112, joystick pad covers the functionality of keypad 204 of FIG. 2A), speaker 113, robotic grasping arms 131 at its stored state (further illustrated in FIGS. 8B-10), electric alarm light 206 for providing warning to the surrounding people regarding actual or impending electric shock, emergency stop button 207 for immediately stopping system 800, self-test button 208, and an accessories storage compartment 804, in which supplemental accessories can be stored such as an atropine and insulin syringes that can be used in corresponding conditions per audial and/or visual instruction and guidance provided by system 800 through display 112 and/or speaker 113.

According to some embodiments of the invention, a remote take-over by medically skilled personnel is enabled (i.e., computer 110 is adapted to authorize such a take-over through smartphone 111 or alternate communication means), thereby the remote medical personnel can utilize the monitoring capabilities of system 800 (e.g., sensors 102-105 and database 109) to analyze the patient's condition as well as to remotely operate the life-saving devices 121-124 of system 800. During the remote take-over operation, the medical personnel can instruct an occasional treating person as of further life-saving operations as well as to warn the surrounding to clear away when electric shocks to be delivered, by remotely controlling computer 110 and there through, display 112, speaker 113, and alarm light 206.

FIG. 8B schematically illustrates a bottom view of a portable automated life-saving system 800, showing multiple elastic pads 132 (further illustrated in FIG. 11 ergonomically shaped to adapt to the patient's chest), grasping arms 131 at its stored state (further illustrated in FIGS. 9-10), emergency stop button 207, a plurality of ECG leads 211 utilized to acquire detailed ECG monitoring of the patient's cardiac condition, some of which can be utilized as electrodes of defibrillator 122 and pacemaker 124 in lieu of pads 209 of FIG. 2B.

System 800 is adapted with a narrowed and ergonomically shaped piston 210, which is adapted to apply compressions only to the patient's chest bone, thus enabling the chest ribs to remain with most of its volume, thus avoiding undesired excess evacuation of air from the patient's lungs while delivering the required compressions mechanically forcing the patient's heart to retract for building artificial blood pressure.

Further shown in FIG. 8B is an image acquisition device 805 such as a digital camera, which is utilized for proper positioning of system 800 above the patient's chest, for example by initially placing a cross marker label on the patient's chest followed by computer 110 seeks for the matching the detected cross mark with a corresponding virtual alignment mark to enable proper alignment and positioning of system 800. According to some embodiments, system 800 is configured to project alignment marks on the patient's chest (e.g., through corresponding irradiating means).

Chest Holder

Figure 9:
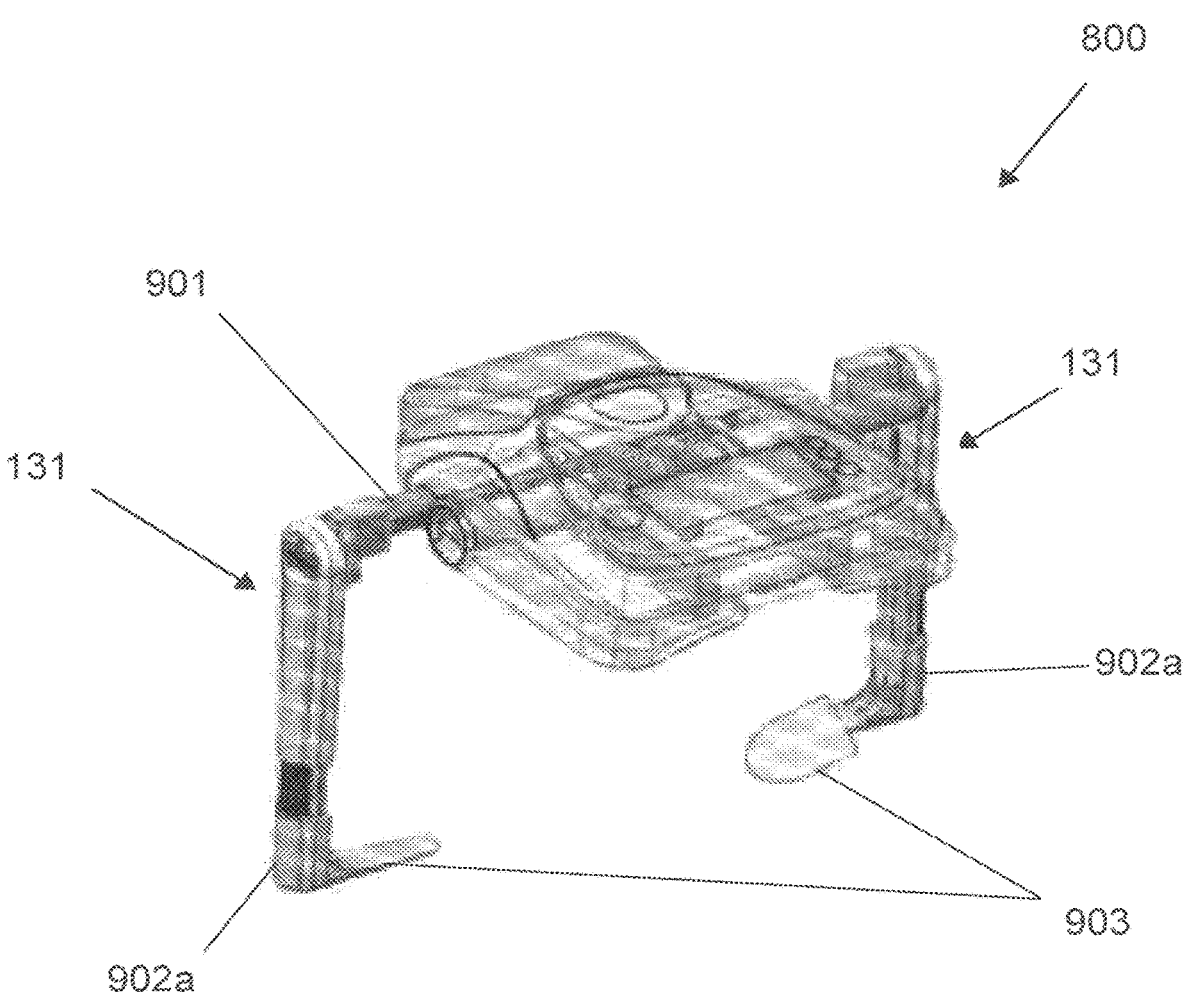
FIG. 9 schematically illustrates a perspective view of the system of FIGS. 8A-8B.

FIG. 9 schematically illustrates a perspective view of system 800, with robotic grasping arms 131 automatically deployed such as to grasp a laying patient (i.e., in a similar manner as illustrated in FIGS. 4-5). Grasping arms are adapted with a lateral extension mechanism 901 (e.g., a rack and pinion arrangement) and with a suitable vertical extension mechanism enabling the vertical extension of the lower portion 902a of arms 131, thereby arms 131 can initially extend laterally to its outermost state, fold down to an essentially vertical position, extend lower potions 902a downwardly until reaching the ground (i.e., utilizing suitable pressure/resistance means to detect the ground touching, followed by retraction steps of the portion 902a of arms 131 which penetrate under the patient back to achieve firm adaption to the patient's body. As a result, the elastic pads 132 are firmly pressed adapting to the patient chest.

According to some embodiments of the invention, lower portions 902a are adapted with conductive pads 903 which are suitable for being utilized as defibrillator pads, thereby enabling the delivery of front to back electric shocks (i.e., one electrode contacts the patient's chest while the opposed electrode contacts the patient's back) which was found to be highly effective than delivering an electric shock with both electrodes contacting the front side, namely the patient's chest.

The automatic deployment and grasping process can simply begin by pressing the self-testing button 208 (FIG. 8A) or automatically as system 800 detects its aligned placement on a patient's chest with the power button 201 pressed. However, system 800 may be configured to identify emergency circumstances where only partial positioning is achieved (e.g., a patient feels distressed, retrieves system 800 of its storage means, such as cabinet 1300 of FIG. 13, and then loses consciousness. In such cases, or in cases where a person is known to be at medical risk, system 800 can be configured to respond to such a partial operation by performing predetermined emergency responses, such as to audial alert and to communicate with predetermined medical assistance personnel.

ECG Sensors

Figure 10:
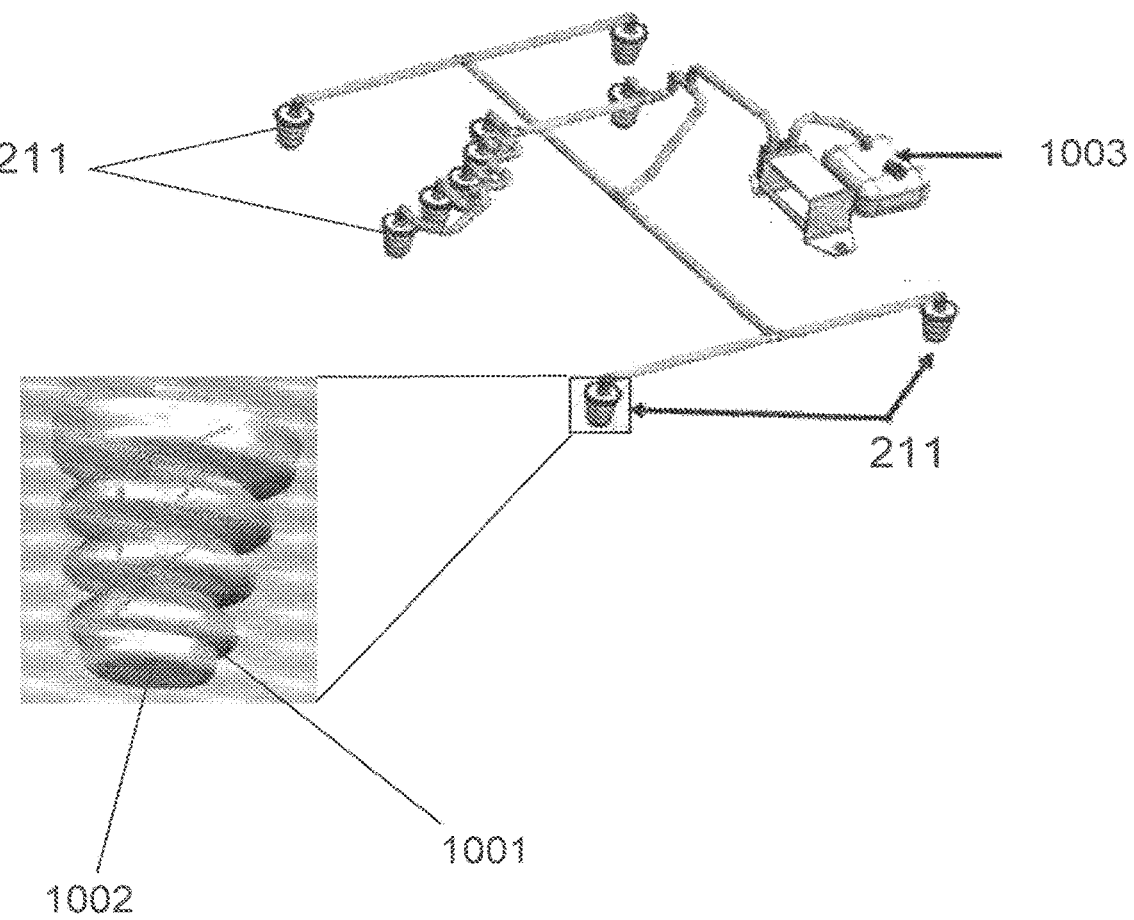
FIGS. 10-11 show extendable elastic pads of the proposed system, according to an embodiment of the invention.

In order to enhance the contact of the ECG leads 211 with the patient's chest, leads 211 are adapted with inflatable elastic leads 1001 shown in FIG. 10, through which the conductive ECG sensors 1002 are wired. When system 800 is adapting to the patient's chest, by elastic pads 132 (FIGS. 8 and 11), computer 110 instructs controller 120 (FIG. 1C) to activate a suitable hydraulic or pneumatic inflation system 1003 to fill inflatable leads 1001 with liquid/gas until reaching a predetermined pressure, in order to achieve sufficient contact between sensors 1002 and the patient's chest.

According to an embodiment of the invention, leads 1001 are adapted with a pressure gauge to verify that no excess pressure is applied onto the patient's chest by leads 211. Upon system 800 is turned off, the hydraulic/pneumatic filling is being emptied from the ECG leads 1001 (e.g., air pressure being equalized with the ambient atmospheric pressure) which elastically retract to its stored state.

Figure 11:
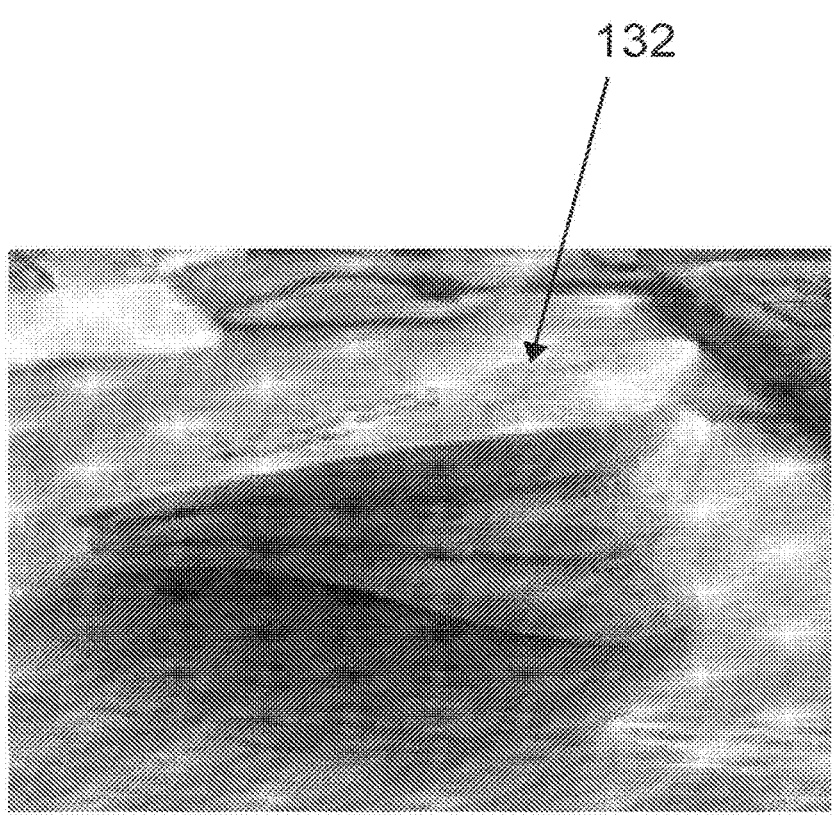

FIG. 11 illustrates elastic spring-like squeezable pads 132, according to an embodiment of the present invention. Elastic pads 132, which are made of biocompatible plastic polymer, are located at the bottom of system 800 (as illustrated in FIG. 8b), for generating an adjustable contact between system 800 and the patient's chest, thus enabling the adaption of system 800 to variable body patterns and sizes.

Figures 12A, 12B:
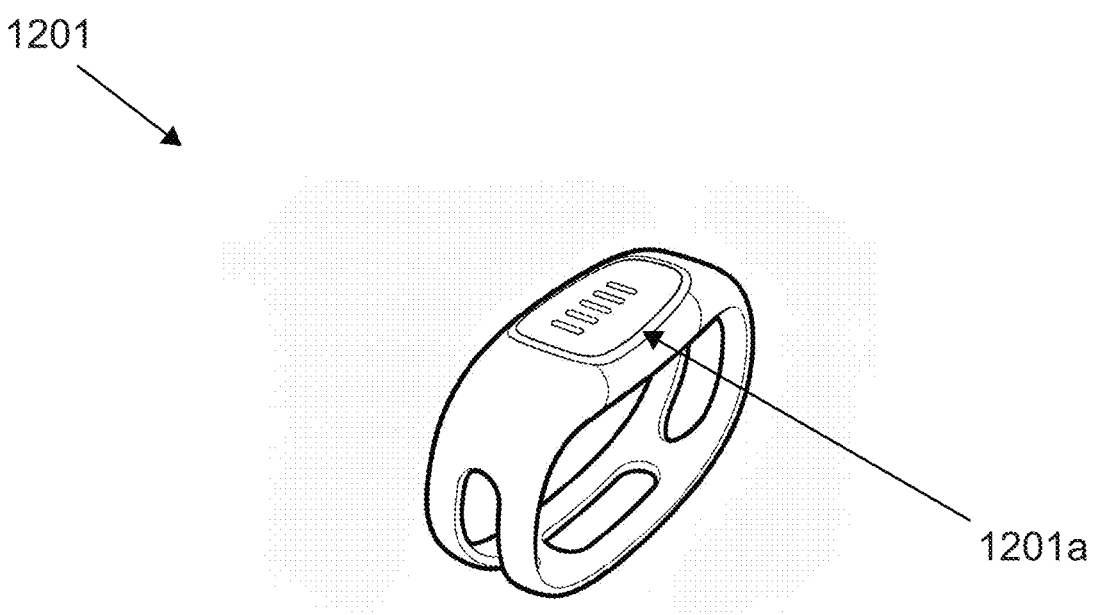
FIGS. 12A-12B shows an independent wearable bracelet and illustrate the use thereof, according to an embodiment of the invention.

FIG. 12A shows an independent monitoring bracelet of a portable automated life-saving system, according to some embodiments of the invention. An independent bracelet 1201 can be utilized independently, provided with pulse sensor and with ECG sensors 102, as well as with communication means (e.g., a cellular transceiver) for communicating with corresponding emergency services upon detecting with its sensors that the wearing person is experiencing an emergency condition. The independent bracelet 1201 can be highly useful, for example, to alert for dangerous sleep apnea events and cradle death in babies.

Bracelet 1201 comprises illuminated indicators 1201a, for providing a visual indication of the sensors' measurements. When the sensed vital signs are within the normal range, the corresponding indicators 1201a are illuminated with a green light), and when sensed vital signs are outside the normal range, the corresponding indicators 1201a are illuminated with a red light).

FIG. 12B schematically illustrates the use of a bracelet 1201 provided with a Bluetooth communication device for communicating with a control box 1202, which comprises cellular communication means 1203 for alerting to an emergency service, and audial alerting means 1204 for sounding an alarm sound upon detecting a medical emergency experienced by one or more persons wearing bracelets 1201. The control box can be mounted to the wall at home, or at swimming pools to urge assistance for distressed swimmers.

Figure 13:
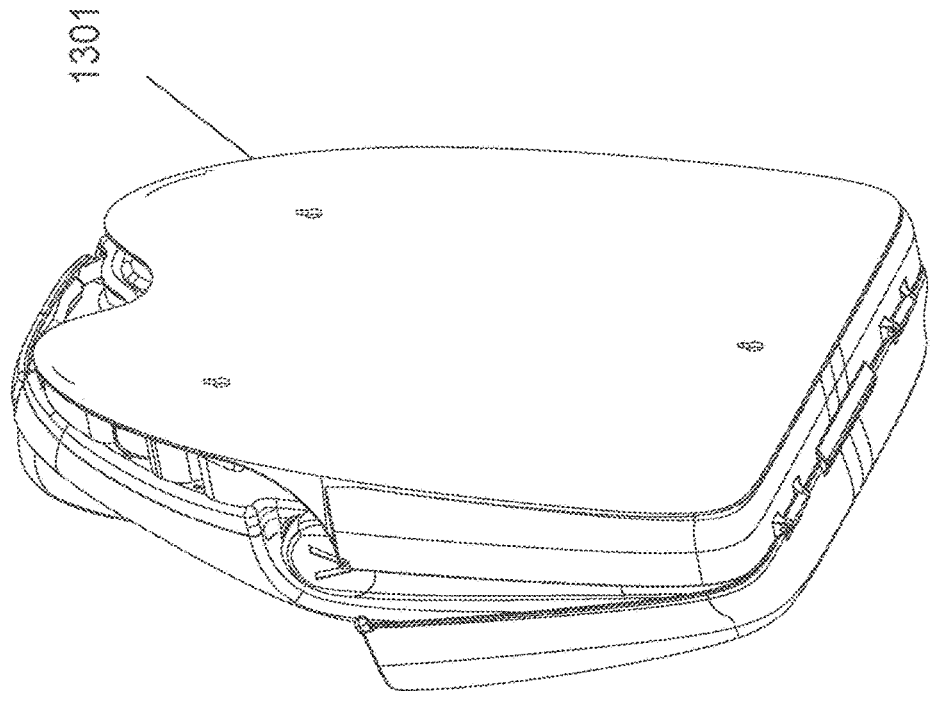
FIG. 13 shows a storage cabinet of the proposed system, according to an embodiment of the invention.
Figure 13:
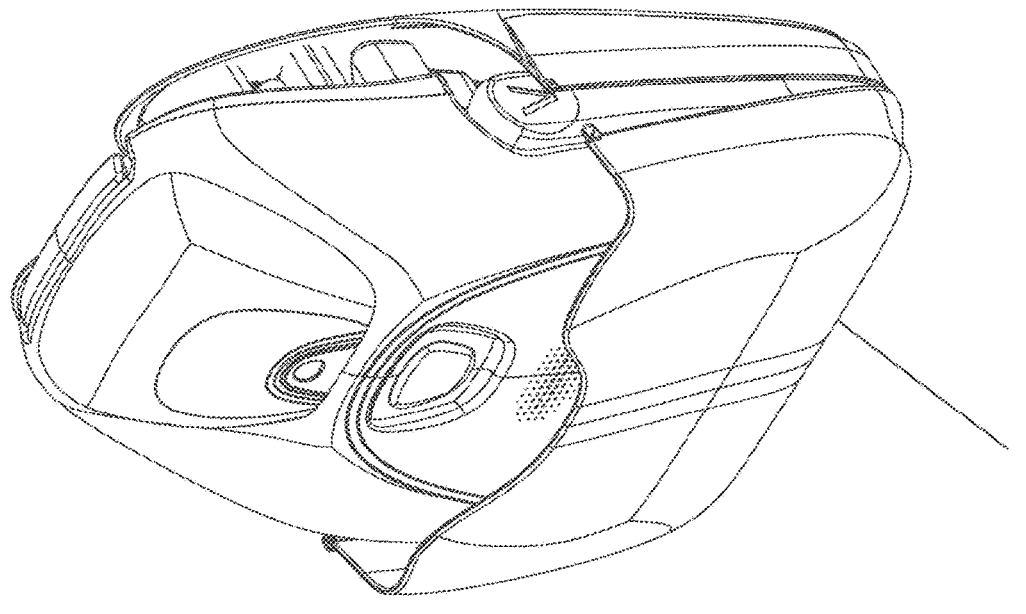

When the proposed system is on standby or turned off, the system is stored in a designed wall cabinet 1300, being illustrated in FIG. 13, from which it can be easily removed (accessible and at an accessible height). The cabinet is plugged in with an electric cable connected to a charger. The proposed system is being routinely checked at a predetermined frequency (for example, once every month) and alerts on detected faults by operating alarming light 206 and through a message sent to predetermined contact persons, e.g., via mobile phones. The test can be performed automatically, or initiated manually, by clicking a designated testing button such as BIT button 202 of FIG. 2A. Each test includes the following:

a. Battery voltage test and low voltage alarm.
b. The heart compression plunger test includes low-pressure activation against a soft cabinet system.
c. Electric market test with the help of a defibrillator—weak market flow in the cabinet.
d. Simultaneous ECG test.
e. Breathing assistance.
f. Closing the system to a simultaneous body in the cabinet.

According to an embodiment of the invention, cabinet 1300 comprises a rear member 1301 adapted to be attached to a construction wall, and a frontal member 1302 which is detachably attached (e.g., hinged) to member 1301 for comfortably removing the proposed system and bringing it to action. Rear member is also adapted with gel sockets being correspondingly positioned with ECG pads 211 (FIG. 10) thus ECG leads 1002 are constantly maintained with a gel layer, thus being ready to provide an improved contact whenever the proposed system is removed from cabinet 1300 for use.

Although embodiments of the invention have been described by way of illustration, it will be understood that the invention may be carried out with many variations, modifications, and adaptations, without exceeding the scope of the claims.

The invention claimed is:

1. A portable automated life-saving system, comprising:
   a) one or more sensors utilized for collecting data related to a patient's current medical condition and to transmit the collected data to a main computer;
   b) a main computer adapted with suitable hardware and software to process data, received from said one or more sensors, with respect to predefined medical conditions and corresponding life-saving treatment protocols, thereby to determine an initial life-saving treatment protocol to be delivered to the patient, and accordingly to operate a main controller configured to activates corresponding life-saving devices;
   c) a main controller adapted to be operated by said main computer, for controllably activating fastening means, and for controllably activating one or more life-saving devices for delivering life-saving treatment to said patient;
   d) two or more fastening means, controllably activated by said main controller for obtaining a firm attachment of said automated life-saving system to a patient;
   e) one or more life-saving devices controllably activated by said main controller for delivering life-saving treatment to said patient; and
   f) one or more batteries,
   wherein said portable automated life-saving system continuously monitors the evolving medical condition of a patient, and correspondingly adapts the given treatment by operating one or more of said life-saving devices.

2. A system according to claim 1, further comprising a database related to the patient's medical history, for enabling more accurate detection of the patient's current medical condition.

3. A system according to claim 1, in which the one or more sensors are selected from the group consisting of: ECG sensors, blood oxygen saturation sensors, blood pressure sensors, Glucose blood levels sensors, or any combination thereof.

4. A system according to claim 1, in which the one or more life-saving devices are selected from the group consisting of: a chest compression device, defibrillator, a breathing assistance device, an external pacemaker, or any combination thereof.

5. A system according to claim 1, in which the main controller controllably activates the life-saving devices by control signals selected from the group consisting of: electrical signals, pneumatic signals, hydraulic signals, or any combination thereof.

6. A system according to claim 1, in which the two or more fastening means comprise at least two grasping arms adapted to laterally grasp underneath a laying patient's body.

7. A system according to claim 1, in which the two or more fastening means comprise one or more inflatable pads, being inflated by pressurized means selected from the group consisting of: pressurized gas container, pneumatic inflation means, hydraulic inflation means, or any combination thereof.

8. A system according to claim 1, further comprising alerting means for guiding a treating person as of required operations, as well as of clearance required before said system discharges an electric shock to a patient, said alerting means are selected from the group consisting of: audial warning, visual warning, or a combination thereof.

9. A system according to claim 1, in which the one or more sensors are connected to communicate with said system by connection means selected from the group consisting of: wired connection, Bluetooth connection, Wifi connection, or any combination thereof.

10. A system according to claim 1, further comprising one or more of the following:
   connection ports selected from the group consisting of: USB port, memory card reader port, Ethernet port, or any combination thereof;
   a memory card reader;
   an Ethernet connection port.

11. A system according to claim 1, further comprising remote communication means for contacting medical assistance and other predetermined contacts.

12. A system according to claim 11, in which the remote communication means are selected from the group consisting of: Cellular communication device, Wifi communication device, or any combination thereof.

13. A system according to claim 3, in which the ECG sensors are integrated with the two or more fastening means.

14. A system according to claim 3, in which one defibrillator electrode contacts the patient's chest, while a second defibrillator electrode contacts the patient's back, thus enabling the generation of electric shock from opposed sides of the heart.

15. A system according to claim 1, further comprising:
   a) a mobile phone application for allowing remote exchange of data and control signals with external servers;
   b) a blood pressure cuff for allowing patient's blood pressure measurements; and
   c) an external remote control for remote system operation, changing telephone numbers and receiving faults.

16. A system according to claim 1, in which the adjustment mechanism comprises lateral rails and longitudinal rods for adjusting the displacement of the fastening means.

17. A system according to claim 1, in which the main computer is adapted to continuously record the ongoing medical condition of a patient.

18. A system according to claim 1, further comprising a self-test operation enabling a user to test his condition.

19. A system according to claim 1, further comprising wall cabinet for storage when said system is not in use, wherein said wall cabinet is adapted with gel sockets correspondingly positioned for maintaining ECG leads of said system lubricated with a gel layer.

20. A system according to claim 1, in which at least one of the one or more sensors are embedded within a wearable bracelet.

* * * * *